(12) United States Patent
Christoph

(10) Patent No.: US 7,008,939 B2
(45) Date of Patent: Mar. 7, 2006

(54) USE OF WEAK OPIOIDS AND MIXED OPIOID AGONISTS/ANTAGONISTS FOR TREATMENT OF URINARY INCONTINENCE

(75) Inventor: Thomas Christoph, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/448,322

(22) Filed: May 30, 2003

(65) Prior Publication Data
US 2004/0029905 A1    Feb. 12, 2004

Related U.S. Application Data

(63) Continuation of application No. PCT/EP01/13911, filed on Nov. 28, 2001.

(30) Foreign Application Priority Data
Nov. 30, 2000    (DE) ............................... 100 59 415

(51) Int. Cl.
A61K 31/55    (2006.01)
A61K 31/44    (2006.01)
A61K 31/24    (2006.01)

(52) U.S. Cl. .................. 514/212.01; 514/282; 514/538

(58) Field of Classification Search ........... 514/212.01, 514/282, 538
See application file for complete search history.

(56) References Cited

U.S. PATENT DOCUMENTS

| | | | |
|---|---|---|---|
| 5,354,863 A | 10/1994 | Dappen et al. | |
| 5,840,696 A | 11/1998 | Lippton | |
| 5,859,043 A | 1/1999 | Kapusta | |
| RE36,547 E * | 2/2000 | Crain et al. | 514/282 |
| 6,159,501 A * | 12/2000 | Skinhoj | 424/461 |
| 2003/0166670 A1 * | 9/2003 | Brooks-Korn | 514/282 |

FOREIGN PATENT DOCUMENTS

| | | |
|---|---|---|
| DE | 19947747 | 4/2001 |
| EP | 0913152 | 5/1999 |
| WO | WO 93/15062 | 8/1993 |
| WO | WO 98/46216 | 10/1998 |
| WO | WO 99/22737 | 5/1999 |

OTHER PUBLICATIONS

Dray et al., "Meptazinol: Unusual In Vivo Opioid Receptor Activity at Supraspinal and Spinal Sites", *Neuropharmacology*, vol. 25, No. 4 (1986), pp. 343-349.
JP 07053534 A, Patent Abstracts of Japan, no date available.
Parfitt, Martindale—*The Complete Drug Reference—Thirty-Second Edition*, Pharmaceutical Press, 1999, pp. 26-29, 34, 52-53, and 89.
Murray, "Acute Urinary Retention Associated with Sublingual Buprenorphine", *British Medical Journal*, vol. 286, No. 6367 (1983), pp. 763-764.
Malinovsky et al., "The Urodynamic Effects of Intravenous Opioids and Ketoprofen in Humans", *Anesthesia and Analgesia*, vol. 87, No. 2 (1998), pp. 456-461.
Fowler et al., "Effects of Liquid Diphenoxylate Hydrochloride and Atropine Sulfate (Lomotil) Instillations on Dynamics and Function of Continent Cecal Urinary Reservoirs", *The Journal of Urology*, vol. 138, No. 4 (1987), pp. 735-738.
Aceto et al., "Stereoselective Mu- and Delta-Opioid Receptor-Related Antinociception and Binding with (+)-Thebaine" (Abstract), PubMed Database, National Library of Medicine, no date available.
Speigel et al., "Meptazinol a Novel Mu-1 Selective Opioid Analgesic" (Abstract), Biosis Database, no date available.
Elwood, "Sticky Business: Patterns of Procurement and Misuse of Prescription Cough Syrup in Houston", *Journal of Psychoactive Drugs*, vol. 33, No. 2 (2001), pp. 121-133.

* cited by examiner

Primary Examiner—Raymond J. Henley, III
(74) Attorney, Agent, or Firm—Crowell & Moring LLP

(57) ABSTRACT

A pharmaceutical composition for the treatment of an increased urge to urinate or urinary incontinence, comprising an effective amount of at least a compound selected from the group consisting of codeine, dihydrocodeine, dextropropoxyphene, meptazinol and tilidine. Also disclosed are methods of treatment using the pharmaceutical compositions and preferred dosages for the treatment methods.

17 Claims, No Drawings

USE OF WEAK OPIOIDS AND MIXED OPIOID AGONISTS/ANTAGONISTS FOR TREATMENT OF URINARY INCONTINENCE

CROSS REFERENCE TO RELATED APPLICATIONS

The present application is a continuation of International Patent Application No. PCT/EP01/13911, filed Nov. 28, 2001, designating the United States of America and published in German as WO 02/43713 A2, the entire disclosure of which is incorporated herein by reference. Priority is claimed based on Federal Republic of Germany Patent Application No. 100 59 415.8, filed Nov. 30, 2000.

FIELD OF THE INVENTION

The invention relates to the use of weak opioids and mixed opioid agonists/antagonists for the preparation of a medicament for the treatment of an increased urge to urinate or urinary incontinence, and to corresponding medicaments and methods for treatment of an increased urge to urinate or urinary incontinence.

BACKGROUND OF THE INVENTION

Urinary incontinence is the involuntary discharge of urine. This occurs in an uncontrolled manner when the pressure within the urinary bladder exceeds the pressure needed to close the ureter. Causes can be on the one hand an increased internal pressure in the bladder (e.g. due to detrusor instability) with the consequence of urgency incontinence and on the other hand a reduced sphincter pressure (e.g. following giving birth or surgical interventions) with the consequence of stress incontinence. The detrusor is the coarsely bundled multilayered bladder wall musculature, contraction of which leads to discharge of urine, and the sphincter is the closing muscle of the urethra. Mixed forms of these types of incontinence and so-called overflow incontinence (e.g. in cases of benign prostate hyperplasia) or reflex incontinence (e.g. following damage to the spinal cord) occur. Further details in this respect are to be found in Chutka, D. S. and Takahashi, P. Y., 1998, drugs 560: 587–595.

The urge to urinate is the state, aimed at discharge of urine (miction), of increased bladder muscle tension as the bladder capacity is approached (or exceeded). This tensioning acts here as a stimulus to miction. An increased urge to urinate is understood here as meaning in particular the occurrence of a premature or increased and sometimes even painful urge to urinate up to so-called strangury. This consequently leads to significantly more frequent miction. Causes can be, inter alia, inflammations of the urinary bladder and neurogenic bladder disorders, and bladder tuberculosis. However, all causes have not yet been clarified.

An increased urge to urinate and urinary incontinence are extremely unpleasant and there is a clear need among persons afflicted by these conditions to achieve an improvement which is as long-term as possible.

An increased urge to urinate and in particular urinary incontinence are conventionally treated with medicaments using substances which are involved in the reflexes of the lower urinary tract (Wein, A. J., 1998, Urology 51 (suppl. 21): 43–47). These are usually medicaments which have an inhibiting action on the detrusor muscle, which is responsible for the internal pressure in the bladder. These medicaments are e.g. parasympatholytics, such as oxybutynin, propiverine or tolterodine; tricyclic antidepressants, such as imipramine; or muscle relaxants, such as flavoxate. Other medicaments, which in particular increase the resistance of the urethra or of the neck of the bladder, show affinities for $\alpha$-adrenoreceptors, such as ephedrine, for $\beta$-adrenoreceptors, such as clenbutarol, or are hormones, such as oestradiol.

Certain diarylmethylpiperazines and -piperidines are also described for this indication in WO 93/15062. For tramadol also a positive effect on bladder function has been demonstrated in a rat model of rhythmic bladder contractions (Nippon-Shinyaku, WO 98/46216). The literature furthermore contains studies on characterization of the opioid side effect of urine retention, which give some indications of the influence on bladder functions by weak opioids, such as diphenoxylate (Fowler et al., 1987 J. Urol 138:735–738) and meperidine (Doyle and Briscoe, 1976 Br J Urol 48:329–335), by mixed opioid agonists/antagonists, such as buprenorphine (Malinovsky et al., 1998 Anesth Analg 87:456–461; Drenger and Magora, 1989 Anesth Analg 69:348–353), pentazocine (Shimizu et al. (2000) Br. J. Pharmacol. 131 (3):610–616) and nalbuphine (Malinovsky et al., 1998, loc. cit.), and by potent opioids, such as morphine (Malinovsky et al., 1998 loc. cit.; Kontani and Kawabata, (1988); Jpn J Pharmacol. Sep;48(1):31) and fentanyl (Malinovsky et al., 1998 loc. cit.). However, these studies were usually conducted in analgesically active concentrations.

In the case of the indications in question here, however, it should be remembered that it is in general a matter of very long-term uses of medicaments and, in contrast to many situations where analgesics are employed, those affected are faced with a situation which is very unpleasant but not intolerable. It is therefore to be ensured here—even more so than with analgesics—that side effects are avoided if the person affected does not want to exchange one evil for another. Also, analgesic actions are also largely undesirable during permanent treatment of urinary incontinence.

DESCRIPTION OF THE INVENTION

The object of the present invention was therefore to discover substances which are helpful for treatment of an increased urge to urinate or urinary incontinence and at active doses preferably simultaneously show fewer side effects and/or analgesic actions.

Surprisingly, it has now been found that certain weak opioids and mixed opioid agonists/antagonists have an outstanding action on bladder function at low concentrations and accordingly are particularly suitable for treatment of corresponding diseases.

The invention accordingly provides the use of one of the following compounds
  codeine or dihydrocodeine,
  dextropropoxyphene,
  meptazinol or
  tilidine as free base and/or in the form of physiologically acceptable salts for the preparation of a medicament for treatment of an increased urge to urinate or urinary incontinence.

Surprisingly, it has been found that these compounds significantly improve physiological parameters which are of importance in cases of an increased urge to urinate or urinary incontinence, in particular in areas of a reduction in the interval of rhythmic bladder contraction. This change can mean a significant alleviation of symptoms.

Suitable salts in the context of this invention and in each of the uses claimed are salts of the particular active compound with inorganic or organic acids and/or a sugar substitute, such as saccharin, cyclamate of acesulfam. However, the hydrochloride is particularly preferred.

Codeine ((5a,6a)-7,8-didehydro-4,5-epoxy-3-methoxy-17-methylmorphinan-6-ol) is an active compound with an antitussive, narcotic and analgesic action. It is described in the German Reichspatent (DRP) 247 180 to C. H. Boehringer of 1912.

Dihydrocodeine ((5a,6a)-4,5-epoxy-3-methoxy-17-methylmorphinan-6-ol) is used as an analgesic and antitussive and is described by Stein, A.: Pharmazie (PHARAT) 10, 180 (1955).

Dextropropoxyphene ([S-(R*,S*)][-a-[2-(dimethylamino)-1-methylethyl]-a-phenylbenzene-ethanol propanoate (ester)) is an analgesic described in U.S. Pat. No. 2 728 779.

Meptazinol (3-(3-ethylhexahydro-1-methyl-1H-azepin-3-yl)phenol), a narcotic and analgesic, is described in DE-OS 1 941 534 or GB 1 285 025.

Tilidine (trans-2-(dimethylamino)-1-phenyl-3-cyclohexene-1-carboxylic acid ethyl ester) is described in DE 1 518 959 or U.S. Pat. No. 3,557,126 and is a known analgesic and narcotic.

The use of dextropropoxyophene, codeine, meptazinol or tilidine is preferred in particular for the preparation of the medicament. In particular codeine, meptazinol or tilidine is preferred.

In a preferred embodiment according to the invention codeine is used, preferably in the form of the free base, the HBr or HI salt or as codeine phosphate.

In a preferred embodiment according to the invention tilidine is used, preferably in the form of the free base or the HCl salt, also in the form of its racemates; enantiomers, diastereomers, in particular mixtures of the enantiomers or diastereomers, or of an individual enantiomer or diastereomer.

In a preferred embodiment according to the invention meptazinol is used, preferably in the form of the free base or the HCl salt, also in the form of its racemates; enantiomers, diastereomers, in particular mixtures of the enantiomers or diastereomers, or of an individual enantiomer or diastereomer.

In a preferred embodiment according to the invention dihydrocodeine is used, preferably in the form of the free base or as dihydrocodeine tartrate.

In a preferred embodiment according to the invention dextropropoxyphene is used, preferably in the form of the free base, the HCl salt or the napsylate, also in the form of its racemates; enantiomers, diastereomers, in particular mixtures of the enantiomers or diastereomers, or of an individual enantiomer or diastereomer.

Although the uses according to the invention merely display mild side effects, it may also be of advantage, for example to avoid certain forms of dependency, also to use, in addition to these compounds morphine antagonists, in particular naloxone, naltrexone and/or levallorphan. A preferred example would be tilidine and naloxone.

The invention also relates to medicaments for treatment of an increased urge to urinate or urinary incontinence which comprise as the active compound at least one of the compounds chosen from
 codeine or dihydrocodeine,
 dextropropoxyphene,
 meptazinol or
 tilidine
as the free base and/or in the form of physiologically acceptable salts, and optionally additives and/or auxiliary substances.

Suitable salts in the context of this invention and in each of the uses claimed are salts of the particular active compound with inorganic or organic acids and/or a sugar substitute, such as saccharin, cyclamate or acesulfam. However, the hydrochloride is particularly preferred.

Suitable additives and/or auxiliary substances in the context of this invention are substances known to one of ordinary skill in the art for achieving pharmaceutical formulations. The choice of these auxiliary substances and the amounts thereof to be employed depend on whether the medicament is to be administered orally, intravenously, intraperitoneally, intradermally, intramuscularly, intranasally, buccally or locally. Formulations in the form of tablets, chewable tablets, coated tablets, capsules, granules, drops, juices or syrups are suitable for oral administration, and solutions, suspensions, easily reconstitutable dry formulations and sprays are suitable for parenteral, topical and inhalatory administration. Suppositories for use in the rectum are a further possibility. The use in a depot in dissolved form, a carrier film or a patch, optionally with the addition of agents which promote penetration of the skin, are examples of suitable percutaneous administration forms. Examples of auxiliary substances and additives for oral administration forms are disintegrants, lubricants, binders, fillers, mould release agents, where appropriate solvents, flavouring substances, sugar, in particular carrier agents, diluents, dyestuffs, antioxidants etc. Waxes or fatty acid esters, inter alia, can be used for suppositories, and carrier substances, preservatives, suspension auxiliaries etc. can be used for compositions for parenteral administration. The amounts of active compound to be administered to patients vary according to the weight of the patient, the mode of administration and the severity of the disease. The compounds according to the invention can be released in a delayed manner from formulation forms which can be used orally, rectally or percutaneously. Appropriate sustained release formulations, in particular in the form of a "once daily" preparation which has to be taken only once a day, are particularly preferred for the indication according to the invention.

Medicaments which comprise at least 0.05 to 90.0% of the active compound, in particular low active dosages, in order to avoid side effects or analgesic actions, are furthermore preferred.

Preferably, in the use according to the invention of the substances for a medicament for urinary incontinence or for a medicament comprising these active compounds, a dose which is lower than that necessary for an analgesic action is employed in the medicament, that is to say dosages below the analgesic action are used. Dosages between the lower limit of the dose used for pain treatment and 10% of this dose are usual, preferably between 80% and 20% of this dose, in particular between 50 and 30%.

For the opioids, the following concrete doses per administration are preferably employed:

TABLE I

Preferred Dosages

| Substance | Human dose [mg] | | | Dose [µg/kg] | | |
|---|---|---|---|---|---|---|
| | usual | preferred | more preferred | usual | preferred | more preferred |
| Codeine | 4–40 | 8–32 | 12–20 | 62–616 | 123–493 | 185–308 |
| Dextropro-poxyphene | 10–100 | 20–80 | 30–50 | 154–1540 | 308–1232 | 462–770 |
| Meptazinol | 5–50 | 10–40 | 15–25 | 77–770 | 154–616 | 231–385 |
| Tilidine | 5–50 | 10–40 | 15–25 | 77–770 | 154–616 | 231–385 |

Auxiliary substances can be, for example: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatine, sorbitol, inositol, mannitol, microcrystalline cellulose, methylcellulose, carboxymethylcellulose, cellulose acetate, shellac, cetyl alcohol, polyvinylpyrrolidone, paraffins, waxes, naturally occurring and synthetic gums, acacia gum, alginates, dextran, saturated and unsaturated fatty acids, stearic acid, magnesium stearate, zinc stearate, glyceryl stearate, sodium lauryl sulfate, edible oils, sesame oil, coconut oil, groundnut oil, soya bean oil, lecithin, sodium lactate, polyoxyethylene and -propylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talc, kaolin, pectin, crospovidone, agar and bentonite.

The medicaments and pharmaceutical compositions according to the invention are prepared with the aid of means, devices, methods and processes which are well-known in the prior art of pharmaceutical formulation, such as are described, for example, in "Remington's Pharmaceutical Sciences", ed. A. R. Gennaro, 17th ed., Mack Publishing Company, Easton, Pa. (1985), in particular in part 8, chapter 76 to 93.

Thus for a solid formulation, such as a tablet, the active compound of the medicament can be granulated with a pharmaceutical carrier, e.g. conventional tablet constituents, such as maize starch, lactose, sucrose, sorbitol, talc, magnesium stearate, dicalcium phosphate or pharmaceutically acceptable gums, and pharmaceutical diluents, such as water, in order to form a solid composition which comprises a compound according to the invention or a pharmaceutically acceptable salt thereof in homogeneous distribution. Homogeneous distribution is understood here as meaning that the active compound is distributed uniformly over the entire composition, so that this can easily be divided into unit dose forms, such as tablets, pills or capsules, having the same action. The solid composition is then divided into unit dose forms.

The tablets or pills of the medicament according to the invention or of the compositions according to the invention can also be coated or compounded in order to provide a dose form with delayed release. Suitable coating agents are, inter alia, polymeric acids and mixtures of polymeric acids with materials such as e.g. shellac, cetyl alcohol and/or cellulose acetate.

Medicaments which comprise dextropropoxyophene, codeine, meptazinol or tilidine are preferred, particularly those that comprise codeine, meptazinol or tilidine.

Although the medicaments according to the invention merely display mild side effects, it may be of advantage, for example to avoid certain forms of dependency, also to use, in addition to the active ingredient one or more morphine antagonists, in particular naloxone, naltrexone and/or levallorphan. A preferred example would be tilidine or naloxone.

The invention also relates to a method for treatment of an increased urge to urinate or urinary incontinence in which codeine or dihydrocodeine, dextropropoxyphene, meptazinol, pethidine or tilidine in the form of their bases and/or salts of physiologically acceptable acids, optionally also in the form or their racemates, enantiomers, diastereomers, mixtures of enantiomers or diastereomers, or of an individual enantiomer or diastereomer, are used.

The following examples are intended to illustrate the invention without limiting it thereto.

EXAMPLES

Example 1

Test System of Cystometry on Anaesthetized Naïve Rats

The cystometric investigation of naïve female rats was carried out by the method of Kimura et al. (Kimura et al., 1996, Int. J. Urol. 3:218–227). The abdomen of anaesthetized ventilated rats is opened up and the ureter is tied off. The urine is drained from the kidneys. A catheter is inserted into the bladder and fixed. Saline is infused into the bladder via this by means of an infusion pump, until the bladder shows rhythmic spontaneous activity in the form of contractions, which can be recorded via a connected pressure transducer. After stable starting values are reached, the test substance is administered i.v. in a cumulative manner. An influence on bladder function manifests itself via suppression of spontaneous contractions. The absence of contractions over a period of 10 min is used as an indication of suppression.

A suppression of spontaneous contractions in the rats was measurable with all the substances tested. Table II indicates the mean of the lowest dose of 3 independent experiments at which for the first time contractions are absent over a period of 10 min.

TABLE II

Lowest Dose Effective for Suppression of Contraction

| Compound | Lowest dose (mg/kg) |
| --- | --- |
| Tilidine | 0.5 (n = 3) |
| Meptazinol | 1.0 (n = 3) |
| Codeine (phosphate) | 4.7 (n = 3) |

Note:
n corresponds to the number of experiments used to calculate the value.

The substances investigated show a positive action on bladder regulation and are thus suitable for treatment of urinary incontinence.

Example 2

Parenteral Administration Form 38.5 g meptazinol HCl is dissolved in 1 l of water for injection at room temperature and the solution is then adjusted to isotonic conditions by addition of anhydrous glucose for injection.

For an average patient of approx. 65 kg body weight, for example, 0.5 ml of this solution is administered, which corresponds to 19.25 mg or ≈300 µg/kg. The dose can be administered about 3 times daily.

Example 3

Liquid Oral Administration Form as a Combination with Naloxone 23.82 g tilidine HCl ½ H$_2$O and 2.04 g naloxone HCl 2H$_2$O are dissolved in 874 ml purified water, 124 ml ethanol (96%) and 2 ml HCl at room temperature.

For an average patient of approx. 65 kg body weight, 20 drops (≈0.72 ml) of this solution are taken, that is to say 17.15 mg of active compound (corresponds to approx. 16.7 mg tilidine HCl) or 264 µg/kg. This can be taken up to 4 times daily in total.

Example 4

Solid Oral Sustained Release Administration Form (Sustained Release Capsules)

Each sustained release capsule contains:

| | |
| --- | --- |
| 50 mg | dextropropoxyphene HCl |
| 80 mg | Avicel PH 101 |
| 20 mg | lactose monohydrate |
| 12 mg | Eudragit RS |
| 3 mg | Eudragit RL |
| 3 mg | triethyl citrate |
| 5 mg | talc |
| 173 mg | total |

Dextropropoxyphene HCl, microcrystalline cellulose and lactose are mixed homogeneously in a mixer and the mixture is then granulated with water. The moist granules are extruded in a screw extruder with a 0.8 mm (hole diameter) perforated plate and then rounded to pellets in a spheronizer. The pellets are dried in a drying cabinet overnight at 45° C.

The graded pellets of grain class 800–1,200 µm are coated with an aqueous dispersion of Eudragit RS 30D+Eudragit RL 30D, containing tiethyl citrate as a plasticizer and talc as an anti-stick agent, (solids content of the ready-to-use dispersion: 20% w/w) in a fluidized bed coater at a product temperature of approx. 30° C. and then dried for 24 h at 45° C. in a drying cabinet. The pellets are transferred to hard gelatine capsules of size 1 at individual doses of 173 mg.

Dosage: 1 capsule, for a person with a body weight of 65 kg corresponds to about 770 µg/kg. 2 capsules a day are usually taken.

Example 5

Solid Oral Sustained Release Administration Form (Sustained Release Tablets)

Per sustained release tablet:

| | |
| --- | --- |
| 17 mg | codeine phosphate ½ H$_2$O |
| 143 mg | microcrystalline cellulose |
| 94 mg | methylhydroxypropylcellulose 100,000 mPa · s |
| 3 mg | highly disperse silicon dioxide |
| 3 mg | magnesium stearate |
| 260 mg | total |

The auxiliary substances and the active compound are mixed homogeneously in a mixer and the mixture is then pressed on a tablet press to give tablets with a diameter of 9 mm.

Dosage: 1 tablet for a person with a body weight of 65 kg corresponds to about 262 µg/kg. 2 tablets are usually taken.

What is claimed is:

1. A method for the treatment of an increased urge to urinate or urinary incontinence, comprising administering to a patient in need thereof an effective amount of a pharmaceutical composition consisting of
   at least one compound selected from the group consisting of codeine, dihydrocodeine, dextropropoxyphene, meptazinol, tilidine, and pharmaceutically acceptable salts thereof, and
   at least one pharmaceutically acceptable excipient.

2. A method according to claim 1, where the compound is codeine, dextropropoxyphene, meptazinol, or tilidine.

3. A method for the treatment of an increased urge to urinate or urinary incontinence, comprising administering to a patient in need thereof the compound codeine, and a dosage of about 62–616 µg of the compound per kilogram body weight of the patient (µg/kg) is administered.

4. A method according to claim 3, wherein the dosage is about 123–493 µg/kg.

5. A method according to claim 3, wherein the dosage is about 185–308 µg/kg.

6. A method for the treatment of an increased urge to urinate or urinary incontinence, comprising administering to a patient in need thereof the compound dextropropoxyphene, and a dosage of about 154–1,540 µg of the compound per kilogram body weight of the patient (µg/kg) is administered.

7. A method according to claim 7, wherein the dosage is about 308–1,232 µg/kg.

8. A method according to claim 7, wherein the dosage is about 462–770 µg/kg.

9. A method for the treatment of an increased urge to urinate or urinary incontinence, comprising administering to a patient in need thereof the compound meptazinol, and a dosage of about 77–770 µg of the compound per kilogram body weight of the patient (µg/kg) is administered.

10. A method according to claim 9, wherein the dosage is about 154–616 µg/kg.

11. A method according to claim 10, wherein the dosage is about 231–385 µg/kg.

12. A method for the treatment of an increased urge to urinate or urinary incontinence, comprising administering to a patient in need thereof the compound tilidine, and a dosage of about 77–770 µg of the compound per kilogram body weight of the patient (µg/kg) is administered.

13. A method according to claim 12, wherein the dosage is about 154–616 µg/kg.

14. A method according to claim 13, wherein the dosage is about 231–385 µg/kg.

15. A method according to claim 1, wherein said compound is in the form of a racemate.

16. A method according to claim 1, wherein said compound is in the form of a pure enantiomer or diastereomer.

17. A method according to claim 1, wherein said compound is in the form of a mixture of enantiomers or diastereomers.

* * * * *